(12) United States Patent
Freund et al.

(10) Patent No.: US 7,963,921 B1
(45) Date of Patent: Jun. 21, 2011

(54) METHOD AND MEASURING DEVICE FOR DETERMINING BLOOD PRESSURE

(75) Inventors: Dirk Freund, Kelkheim (DE); Fred Schnak, Kronberg (DE); Martin Giersiepen, Oberursel (DE); Frank Kressmann, Schwalbach (DE); Brigitte Harttmann, Niedernhausen (DE)

(73) Assignee: Kaz USA, Inc., Southborough, MA (US)

( * ) Notice: Subject to any disclaimer, the term of this patent is extended or adjusted under 35 U.S.C. 154(b) by 1820 days.

(21) Appl. No.: 09/582,471

(22) PCT Filed: Dec. 23, 1998

(86) PCT No.: PCT/EP98/08429
§ 371 (c)(1),
(2), (4) Date: Aug. 15, 2000

(87) PCT Pub. No.: WO99/33395
PCT Pub. Date: Jul. 8, 1999

(30) Foreign Application Priority Data

Dec. 24, 1997 (DE) .................................. 197 57 974

(51) Int. Cl.
*A61B 5/00* (2006.01)
(52) U.S. Cl. ........................................ 600/485; 600/503
(58) Field of Classification Search .................. 600/490, 600/493–6, 500, 495
See application file for complete search history.

(56) References Cited

U.S. PATENT DOCUMENTS

| 4,338,950 | A | | 7/1982 | Barlow et al. | |
| 4,779,626 | A | | 10/1988 | Peel et al. | |
| 4,870,973 | A | | 10/1989 | Ueno | |
| 4,998,534 | A | * | 3/1991 | Claxton, III et al. | 600/500 |
| 5,040,536 | A | * | 8/1991 | Riff | 600/485 |
| 5,094,293 | A | | 3/1992 | Shinmura | |
| 5,111,826 | A | | 5/1992 | Nasiff | |
| 5,172,696 | A | * | 12/1992 | Souma | 600/473 |
| 5,505,207 | A | | 4/1996 | Abbs et al. | |
| 5,595,359 | A | | 1/1997 | Meneghetti | |
| 5,697,374 | A | | 12/1997 | Odagiri et al. | |
| 5,778,879 | A | * | 7/1998 | Ota et al. | 600/500 |
| 5,895,359 | A | * | 4/1999 | Peel, III | 600/494 |
| 5,906,582 | A | | 5/1999 | Kondo et al. | |
| 6,379,310 | B1 | | 4/2002 | Mori et al. | |
| 6,547,741 | B2 | | 4/2003 | Mori et al. | |

FOREIGN PATENT DOCUMENTS

| DE | 296 12 412 U1 | 7/1996 | |
| DE | 296 12 412.5 | 9/1996 | |
| JP | 58 209 334 | 12/1983 | |
| JP | 61 193 635 | 8/1986 | |
| JP | 62 180 869 | 11/1987 | |
| JP | 63-283625 | 11/1988 | |
| JP | 64-29768 | 1/1989 | |
| JP | 01265 939 | 10/1989 | |
| JP | 01265939 | * 10/1989 | 600/503 |

(Continued)

*Primary Examiner* — Patricia C Mallari
(74) *Attorney, Agent, or Firm* — Stroock & Stroock & Lavan LLP

(57) ABSTRACT

The invention is directed to a method and a device for determining the blood pressure, in which a pressure sensor is applied to an individual's limb to detect the blood pressure prevailing in said limb. According to the present invention, the orientation of the limb is detected by means of an orientation sensing unit, and the detected blood pressure is corrected in an evaluating unit in response to the limb's detected orientation.

9 Claims, 3 Drawing Sheets

FOREIGN PATENT DOCUMENTS

| | | |
|---|---|---|
| JP | 3 221 030 | 9/1991 |
| JP | 5-11902 | 1/1993 |
| JP | 05200 003 | 8/1993 |
| JP | 05200 004 | 8/1993 |
| JP | 07-28063 | 1/1995 |
| JP | 07 143970 | 6/1995 |
| JP | 07 289 527 | 7/1995 |
| JP | 7 275 213 | 10/1995 |
| JP | 07028063 | 8/1996 |
| JP | 08215160 | 8/1996 |
| JP | 08215161 | 8/1996 |
| JP | 08215162 * | 8/1996 ............ 600/500 |
| JP | 08000580 | 9/1996 |
| JP | 9 285 453 | 11/1997 |
| RU | 001807863 | 4/1993 |
| SU | 1477377 A1 | 5/1989 |

* cited by examiner

METHOD AND MEASURING DEVICE FOR DETERMINING BLOOD PRESSURE

This invention relates to a method of determining the blood pressure, in which a pressure sensor is applied to an individual's limb to detect the blood pressure prevailing in said limb and also the orientation of said limb by means of an orientation sensing unit provided in a housing of a blood pressure measuring device. The present invention further relates to a blood pressure measuring device having a pressure sensor for generating a pressure signal, an application unit for applying the pressure sensor to an individual's limb, and an evaluation unit for evaluating the pressure signal, with an orientation sensing unit arranged within a housing of the blood pressure measuring device being provided for sensing the orientation of the limb.

Blood pressure measurements taken from an individual's wrist or finger frequently suffer from lack of measurement accuracy and insufficient repeatability. This is attributable to the high measuring sensitivity with respect to variations in the measurement position, that is, the particular position of an individual's wrist joint or finger relative to the position of the heart. To obtain accurate measurement results, known measuring devices require that the measurement be performed at heart level. However, as a rule this requirement is satisfied only by approximation, being considered restricting and impractical by persons subject to the blood pressure measurement. Therefore the measurements invariably have an inherent inaccuracy. In cases where the measurement site deviates from the heart level, the hydrostatic pressure differential corrupts the measurement result by around 0.78 mm Hg/cm. Hence an improper position during a measurement cycle introduces a systematic error. Moreover, any temporary, rather accidental variation of the position which is caused, for example, by trembling or an arm movement, may introduce a second dynamic error referred to as motion artifact, making it considerably more difficult, if not impossible, to perform the algorithmic evaluation of the actual measured quantity.

In U.S. Pat. No. 4,779,626 it has been proposed providing for compensation of the hydrostatic component of the blood pressure during a blood pressure measurement on a subject's finger by means of a device providing a counterpressure corresponding to the hydrostatic pressure component. To accomplish this, a fluid reservoir connected by means of a tube with the blood pressure measuring device applied to the finger is attached to the subject's chest at heart level. In this arrangement, the pressure sensor of the measuring device is constructed as a differential pressure sensor measuring the pressure differential between the blood pressure in the finger and the fluid pressure at the end of the tube. Obviously, however, this blood pressure measuring device is awkward to handle and requires complicated manipulations for application. In addition, the tube routed along the subject's body impedes that particular subject's freedom of movement.

DE 296 12 412 U1 describes a blood pressure measuring device which is to be applied to an individual's wrist and has a pendulum arranged in the housing of the blood pressure measuring device. The outside of the pendulum is provided with a color scale, causing a specified color to be visible in dependence on the position in which the individual's arm is bent. In this arrangement manipulation is rendered difficult in that, among other reasons, it is first necessary for the pendulum to die out before a readout can be obtained.

It is therefore an object of the present invention to provide a method and a device for determining the blood pressure which affords ease of handling while providing at the same time a high measurement accuracy and sufficient repeatability of the blood pressure measurement.

With regard to the process, this object is accomplished by the present invention in a method of the type initially referred to in that the orientation sensing unit delivers an electrical signal responsive to the detected orientation of the individual's limb, and that this electrical signal is further processed. Owing to the electrical detection of the limb's orientation, a wide variety of further processing options of the electrical signal are possible, affording optimal handling and enhancing the accuracy of blood pressure measurement. The movable component provided in the orientation sensing unit which is, for example, constructed in the manner of a pendulum has a specific natural frequency of oscillation determining a period of oscillation. Depending on the type of movement the patient performs, the orientation sensing unit thus generates an oscillation amplitude of varying magnitude which initially builds up to maximum while requiring a certain time for dying out. Owing to the electrical further processing of the measurement signal, it is thus possible to integrate this signal over time or form an average over the period, so that the signal is attenuated significantly, ultimately enabling it to be read or further utilized because smaller excursions and a shorter dying-out period of the movable element in the orientation sensing unit are produced. Hence this solves a problem which may arise particularly in a very compact orientation sensing unit provided within a housing of a blood pressure measuring device. Further options for further processing the electrical signal will be described hereinafter.

Preferably the detected blood pressure is corrected in an evaluating unit in response to the detected orientation of the individual's limb. With a predetermined alignment of the human body, in particular an upright position of the upper part of the body, the sensing unit is capable of detecting the absolute orientation of the limb in the space, thereby enabling the position of the limb relative to the heart to be determined. Correspondingly, the actual blood pressure measured in the limb may be corrected in response to an electrical orientation signal of the sensing unit, enabling the blood pressure prevailing at heart level to be determined.

According to a preferred embodiment of the present invention, the angular position of the subject's limb, in particular the forearm, is detected by means of an inclination sensor, and the detected blood pressure is corrected in response to said angular position. It is in particular possible to detect the inclination of the forearm relative to the horizontal or vertical, which, with the elbow in a predetermined position, for example, a position in which it rests against the upper part of the body, is a measure of the wrist height and hence of the hydrostatic component of the blood pressure in the wrist.

To enable the signals to be processed in simple manner, it is preferable to detect the orientation of the subject's limb and the blood pressure in said limb one after the other. This enables the orientation and the pressure signal to be processed in succession with sufficient accuracy.

According to another preferred embodiment of the present invention, the orientation of the subject's limb is detected simultaneously with the pressure measurement. This enables the accuracy of measurement to be enhanced because the correaction of the sensed blood pressure can invariably be performed on the basis of the limb's particular position.

In an advantageous further aspect of the present invention, it is possible to detect, while the pressure measurement is being taken, a motion, in particular an acceleration of the limb on which the blood pressure is being measured. The detected blood pressure is then corrected in accordance with the detected motion. This enables temporary position changes as caused by trembling during the measurement to be detected. By calculating from the measured position changes back to the corresponding pressure fluctuations, the effect of motion artifacts may be diminished. It is preferable to detect the limb's orientation and motion continuously.

With regard to the device, the object referred to in the foregoing is accomplished by the invention in a blood pressure measuring device of the type initially referred to in that the orientation sensing unit is capable of delivering, for further processing, an electrical signal responsive to the limb's orientation. This enables oscillations in the orientation sensing unit to be adjusted to accurately specified attenuation characteristics without the disadvantage of having to provide for an elaborate mechanical damping which, to be accurate, requires high manufacturing precision.

The evaluating unit preferably comprises a correcting unit for correcting the pressure signal in response to the detected orientation. The orientation sensing unit produces an electrical signal which corresponds to the orientation and is processed in the correcting unit for correcting the pressure signal.

Advantageously, the orientation sensing unit comprises an inclination sensor which detects the inclination of the individual's limb to which the pressure sensor is applied or the inclination of the application unit which corresponds to the limb's inclination. It is preferable for the inclination sensor to be constructed so that it detects the limb's absolute inclination, that is, the angle relative to the horizontal or vertical. The angle of inclination is a measure of the limb's position.

In accordance with a preferred embodiment of the present invention, provision may be made for a motion sensing unit for detecting a motion, in particular an acceleration of the individual's limb, an electrical motion signal being produced for subsequent processing in the evaluating unit. The motion signal enables the degree of motor activity of the particular individual to be determined. In this way an assessment can be made as to whether the patient is generally in a condition of adequate rest and a meaningful measurement is at all possible.

If the likelihood of an insufficiently accurate result is great, the measurement may then be prevented from taking place, or at least an indication of the low informative value of the measurement may be provided on a display device. Advantageously, the detected pressure signal may be corrected in the correcting unit of the evaluating unit in response to the electrical motion signal.

Preferably, the motion sensing unit comprises the inclination sensor and a differentiating unit connected thereto, which forms the first or second derivative of the inclination signal with respect to time and provides the computed signal as motion signal.

In accordance with a preferred embodiment of the present invention, the orientation sensing unit and the pressure sensor are connected to the evaluating unit via a timing unit. The timing unit which provides for time-responsive transmission of the respective signal to the evaluating unit may be configured as a switching device or multiplexer.

Connected between the switching device and the evaluating unit is at least one analog-to-digital converter. To be able to detect the orientation of the limb simultaneously with the pressure measurement, it is preferable to provide two analog-to-digital converters.

Conveniently, the blood pressure measuring device comprises a storage unit for the storage of reference data. The reference data may be used for adapting the correction values for the pressure signal to the particular user. For example, different reference data records may be stored to accommodate different user sizes.

The pressure measurement may be generally taken from different limbs, for example, on a finger. Preferably, however, the application unit for applying the pressure sensor is constructed to fit an individual's wrist. Determining the pressure on the wrist allows a high accuracy of measurement, in addition to enabling the orientation to be sensed in simple manner.

Embodiments of the present invention will be explained in more detail in the following with reference to the accompanying drawing. In the drawing, FIG. 1 is a schematic view of a blood pressure measuring device in accordance with a preferred embodiment of the present invention, showing the device applied to a person's wrist;

Figure 2:
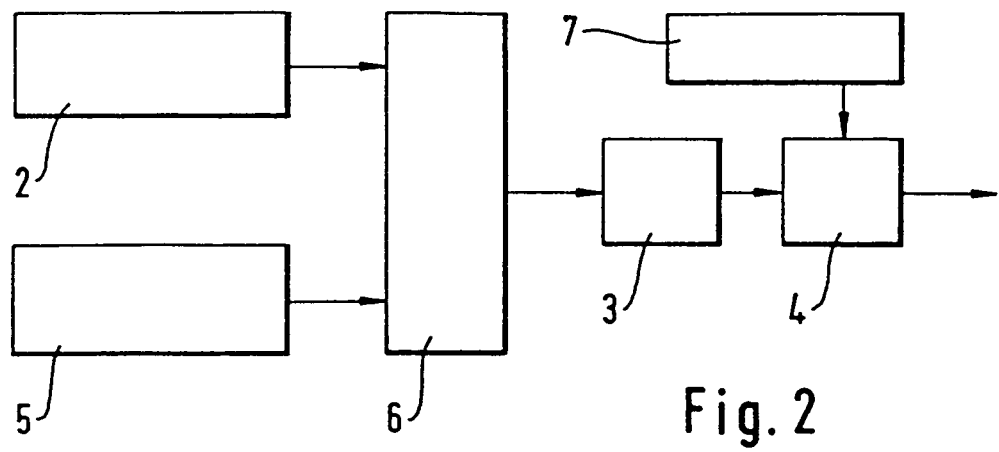
FIG. 2 is a schematic diagram illustrating the constructional features of a preferred embodiment of a blood pressure measuring device of the present invention.
Figure 3:
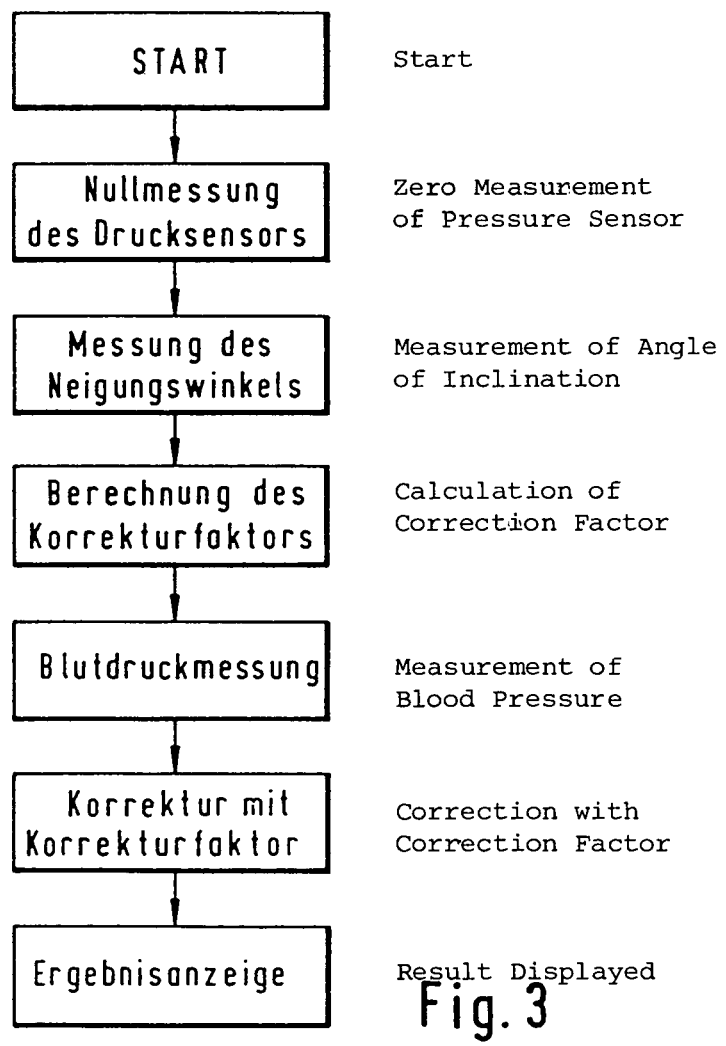
FIG. 3 is a flowchart showing the individual process steps for determining the blood pressure in accordance with a preferred embodiment of the present invention, said process being suitable for implementation with the device of FIG. 2.
Figure 4:
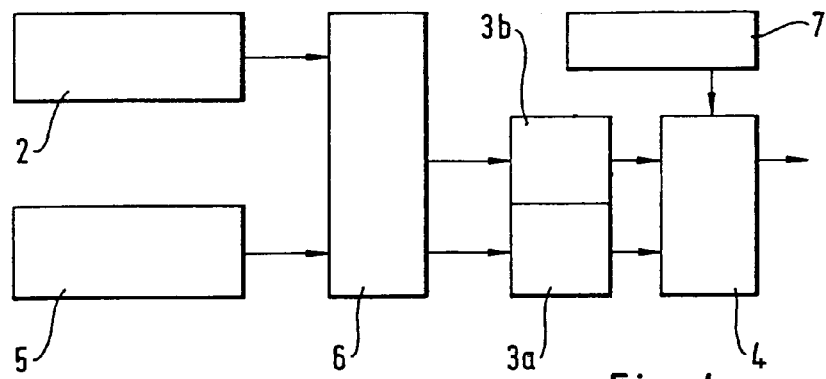
Figure 5:
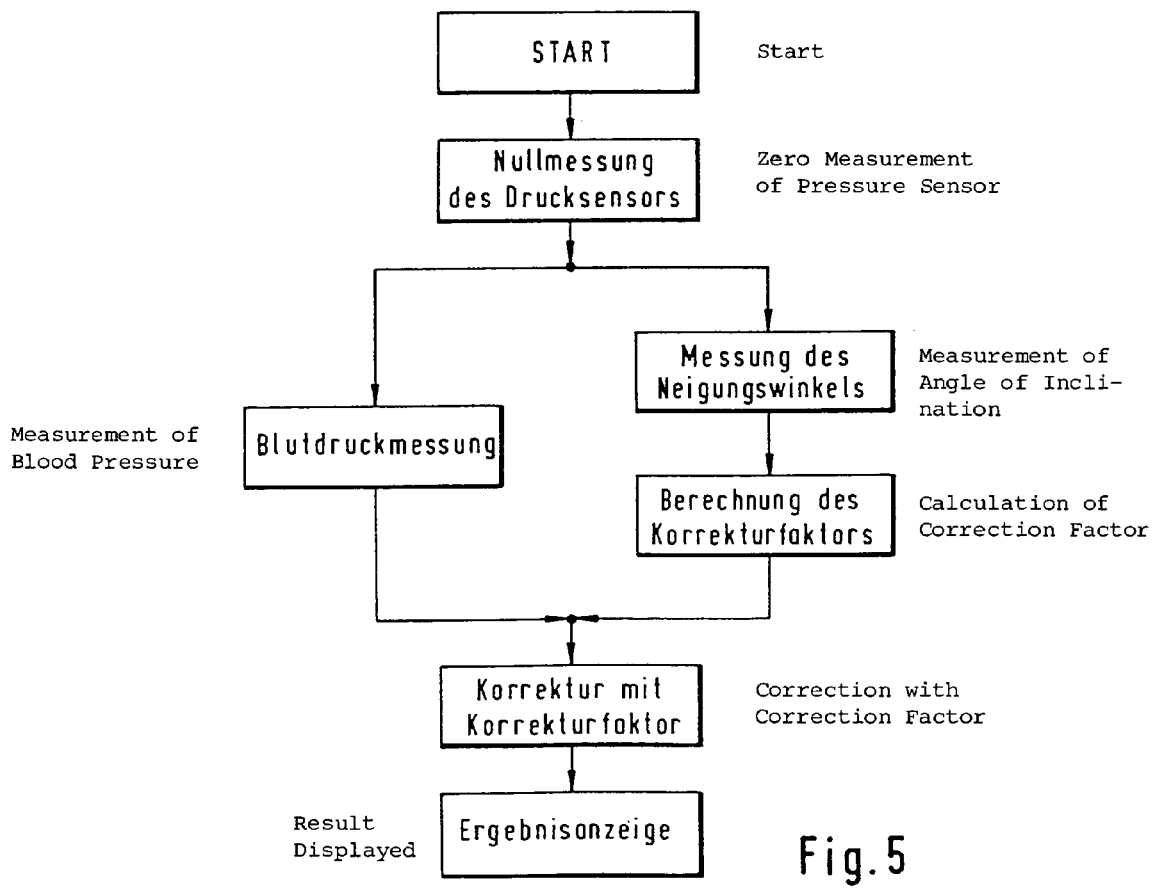

FIG. 4 is a schematic diagram, similar to the one of FIG. 2, illustrating the constructional features of a further embodiment of a blood pressure measuring device of the present invention; and FIG. 5 is a flowchart, similar to the one of FIG. 3, showing the individual process steps for determining the blood pressure in accordance with a further embodiment of the present invention which is suitable for implementation by means of the blood pressure measuring device of FIG. 4.

Figure 1:
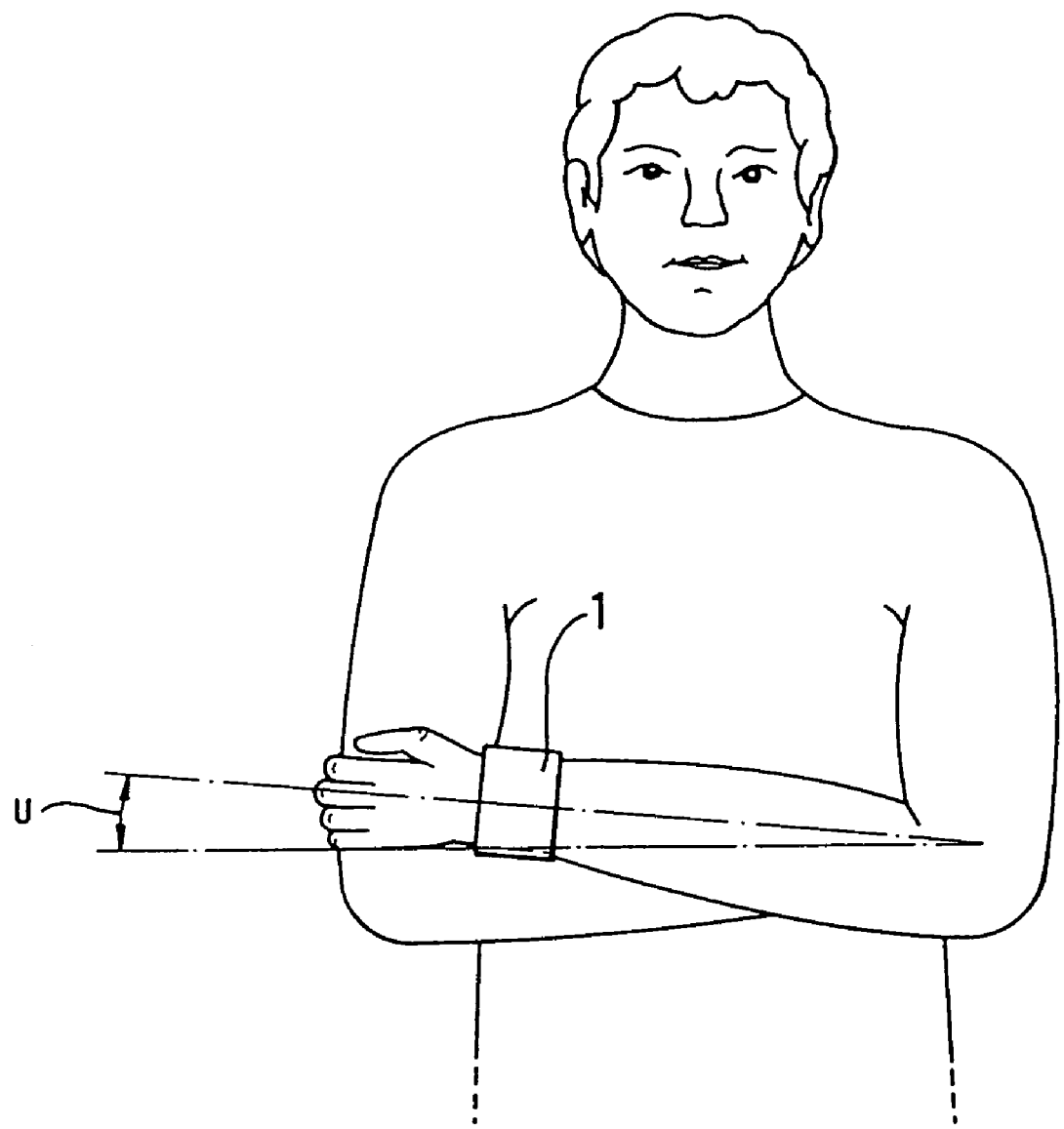

The blood pressure measuring device illustrated in FIG. 1 is constructed to measure the blood pressure on a person's wrist. As application unit it comprises a cuff 1 enabling a pressure sensor to be applied to the inside of the left-hand wrist joint for signal pick-up. The cuff 1 has a bladder inflated preferably with air, the cuff pressure being subsequently decreased for determination of the diastolic, systolic, possibly the mean blood pressure, and the pulse rate by means of the oscillometric method. The pressure sensor 2 (FIG. 2) may be constructed as a capacitive or piezoresistive sensor, for example.

Via an amplifier and analog-to-digital converter 3, the pressure sensor 2 is connected to an evaluating unit 4 which is configured as a microcontroller and for the algorithmic evaluation of the electrical signal of the pressure sensor.

The blood pressure measuring device further comprises an inclination sensor 5 which is likewise connected via the amplifier and analog-to-digital converter 3 to the evaluating unit 4. The inclination sensor 5 detects the inclination of the cuff 1 and hence of the individual's wrist or forearm relative to the horizontal, that is, the inclination sensor 5 provides an electrical signal which corresponds to the wrist's angle of inclination u relative to the horizontal (see FIG. 1). The inclination sensor comprises preferably a movably mounted component, for example, a pendulum, and is provided with a device enabling the angle of inclination u, the speed or the acceleration of the movable component to be detected electrically. Depending on the purpose for which the detected signal is to be used, including for example the distinction between different types of motion artifact, reference is made to the inclination angle, the speed or the acceleration of the movable component. Speed and acceleration of the movable component in the inclination sensor are detectable, for example, by generating the first and second derivative electronically or by employing sensors specifically designed for this purpose, in order to distinguish, for example, between different types of motion artifact and take them into account correspondingly.

As FIG. 2 shows, the pressure sensor 2 and the inclination sensor 5 are connected to the common amplifier and analog-to-digital converter 3 via a timing element 6 which is configured as a multiplexer. The multiplexer 6 selects either the signal of the pressure sensor 2 or the signal of the inclination sensor 5 for onward transmission to the amplifier and analog-to-digital converter 3. The signal processing circuitry shown in FIG. 2 schematically is preferably integrated into a system which, in dependence upon the switching position of the multiplexer 6, also adapts the configuration of the amplifier and analog-to-digital converter 3 to the sensor requirements.

To be able to adapt the blood pressure measuring device to various marginal conditions, in particular various users, provision is made for a reference value storage 7 which is connected to or contained in the evaluating unit 4. The individual marginal conditions of the measurement which influence the positioning of the blood pressure measuring device and hence the measurement result and include, for example, the arm length or the position of the heart, differ among individual users. Therefore, a reference measurement is taken at heart level once, and the results, in particular the detected angle of inclination uref and the signal voltage dependent on this angle, together with calibration data, if any, of the inclination sensor 5, are stored in the reference storage 7 to serve as correcting data for any subsequent blood pressure measurement. The correction of the respective blood pressure measurement results from the measured angle of inclination u as follows:

$P_{korr}=P_{mess}-k(1-\sin u/\sin u_{ref})$, where $P_{korr}$ and $P_{mess}$ are the corrected and, respectively, measured pressure values, u is the angle measured relative to the horizontal position of the blood pressure measuring device, and $u_{ref}$ is the reference angle determined once, equally relative to the horizontal position, with the device placed at heart level. The multiplier k is a constant coefficient required for calibration. In accordance with this relationship it is possible to correct the actual measured pressure by the hydrostatic differential pressure and determine the blood pressure prevailing at heart level. A position-related systematic error is thereby prevented from occurring.

The sequence of process steps during a blood pressure determination will be explained in more detail in the following with reference to FIG. 3. Prior to the measurement proper, a zero measurement of the pressure sensor is performed in order to establish the signal level of the pressure sensor at zero pressure each time again and enhance the accuracy of measurement. As soon as the blood pressure measuring device is applied to the user's left-hand wrist using a cuff 1, the user intending to measure his blood pressure brings his arms into a position substantially folded over the upper part of his body, and his body in an essentially erect position (see FIG. 1). This ensures that the detected angle of inclination u correlates with the position of the wrist relative to the heart, meaning that the angle of inclination u is a measure of the height difference between the position of the wrist and the position of the heart. To ensure a correct position for measurement, the blood pressure measuring device comprises a display device which is preferably arranged such as to be readable by the user only when the proper position is adopted. In particular provision may be made for the display device to be arranged on the upper narrow side of the cuff 1, that is, in the area which, with the cuff applied, is located on the upper narrow side of the joint approximately in extension of the thumb.

Once the user has occupied the proper position, the inclination sensor 5 first operates to determine the angle of inclination u of the blood pressure measuring device. The timing element 6 passes the signal of the inclination sensor 5 on to the amplifier and analog-to-digital converter 3 for evaluation by the evaluating unit 4. In a subsequent process step the correction factor is determined by which the actual measured blood pressure then needs to be corrected. In a further process step the blood pressure prevailing in the wrist is then determined. To this end, the timing element 6 passes the signal of the pressure sensor 2 on to the evaluating unit. Subsequently the actual detected blood pressure is corrected by the previously determined correction value. The corrected blood pressure measurement result is then indicated on the display of the blood pressure measuring device.

Alternatively, it is also possible to control the avoidance of position-related errors via the display of the blood pressure measuring device by user interaction. To this end, the user keeps receiving information on the display of the blood pressure measuring device until after the device is moved within a predetermined angular tolerance range about the reference angle and hence occupies a position in which the blood pressure measurement value is no longer in need of correction or a correction is necessary. In a further embodiment, the information on the display is used for prompting the user to adopt the optimal measurement position at the start of and/or during the pressure measurement cycle. For example, the display produces an arrow pointing in upward and downward direction, with either only the up or the down arrow being indicated or flashing when the user is required to move his wrist, with the blood pressure measuring device attached thereto, in upward or downward direction to reach the proper position for measurement. Another user prompt in the form of a red light for a poor measurement position and/or a green light for a correct measurement position or, alternatively, an audible warning signal produced in the presence of a poor measurement position may also be contemplated as an alternative. Preferably the signal indicative of a correct/incorrect measurement position is displayed on the electronic indicating device (LCD, for example) only prior to the measurement cycle. Alternatively, other instants of time (for example, also during the measurement cycle as in the case of a variation of the measurement position) may be programmed for providing the indication. Because the inclination sensor delivers an electrical signal, limiting the electronic display of the measurement position to specified instants of time, rather than continuously which may irritate the user, poses no problem.

Conversely, in a further embodiment a concrete validation of the measurement results with regard to the detected measurement position is made in a measurement value storage. Thus it is indicated, for example, subsequent to the measurement, whether the measurement result should be disregarded because of an improper measurement position or a movement during the measurement cycle, or whether position-related errors have been compensated for or corrected or eliminated.

It will be appreciated that the embodiments represented in the two preceding paragraphs may be used in combination with the first and also the second embodiment described in the following.

A second embodiment of a blood pressure measuring device of the present invention is illustrated in FIG. 4. The construction of the blood pressure measuring device is generally similar to the one shown in FIG. 2, so that like parts have been assigned like reference numerals and another description of these same parts may be omitted. The embodiment of FIG. 4 differs essentially in the fact that the pressure sensor 2 and the inclination sensor 5 are each separately connected to the evaluating unit 4 via an amplifier and analog-to-digital converter 3a, 3b of their own, rather than being connected to the evaluating unit 4 via a common amplifier and analog-to-digital converter. This enables the signal of the inclination sensor 5 to be made available to the evaluating unit 4 continuously. The angle of inclination u is detected simultaneously with the detection of the blood pressure in the wrist.

To detect a motion or acceleration of the wrist, the evaluating unit 4 comprises a differentiating unit by means of which the derivative, with respect to time, of the signal of the inclination sensor 5, which then corresponds to the motion or (angular) velocity, and the derivative of the derivative with respect to time, which then corresponds to the (angular) acceleration, are determinable.

The sequence of process steps of the method of determining the blood pressure, which may be executed with the device of FIG. 4, is illustrated in FIG. 5. As shown in FIG. 5, the angle of inclination is determined simultaneously with the blood pressure measurement and utilized for computing the correction factor.

From the particular motion (speed) or acceleration of the wrist it is initially determined whether the user is generally in a state of sufficient rest enabling a meaningful measurement to be taken. If an elevated degree of motor activity is established enabling only an unrepresentative blood pressure measurement result to be obtained, the measurement will not take place or the display device will provide an indication of the low informative value of the measurement. It will be understood that this construction of the blood pressure measuring device and this display procedure indicating a low informative value of the measurement due to an unsuitable angular position of the limb to which the blood pressure measuring device is attached or due to particular detected motions which would severely corrupt the measurement result, may be implemented independently of the other correcting and indicating capabilities or in any desired combination. Stopping the measurement or providing an indication of its low informative value may take place before and/or during or after the measurement cycle.

Moreover, the measured blood pressure is corrected by means of the detected motion (speed) and acceleration. Temporary position changes such as brief movements or trembling of the wrist while the blood pressure measurement is being taken primarily enter as fluctuations in the output signal of the pressure sensor. By computing the measured position changes back to the corresponding pressure fluctuation it is possible to diminish the effect of the motion artifacts.

The measurement signal produced by the inclination sensor 5 is further processed preferably electronically, so that attenuated oscillatory characteristics of the movable element in the inclination sensor, including smaller oscillation amplitudes and a shorter dying out period than when generated mechanically, are obtained electronically by filtering, integrating or averaging over the period of the movable element in the pressure sensor. In contrast to mechanical damping systems, this enables optimal attenuation characteristics (also non linear ones) to be adjusted, independent of the manufacturing quality of the movable element in the pressure sensor. This further affords a significantly improved readability of the measured signal on the display device.

The display device on which the processed measurement result of the inclination sensor is indicated is the same device indicating also the blood pressure measurement values and, where applicable, the pulse rate. The device involved is an electronic indicating device of the type including an LCD, ST, STN, TFT or similar display, for example. For example, any type of display is generally usable which is also utilized in connection with indicating devices of portable computers. Since the readability of the visual output of these indicating devices is known to depend on the viewing angle relative to the indicating device, a further embodiment may provide for the measurement result of the inclination sensor to be used in addition or exclusively for adapting the electronic indicating device to the viewing angle in an adapting device, because as a rule a relationship exists between the possible angles of inclination on the wrist and the possible viewing angles relative to the blood pressure measuring device with indicating device on the wrist.

The result of the described zero measurement of the pressure sensor 2 may also be stored in the reference value storage 7, making it necessary to perform a specific calibration only once for each operator and enter only the operator at a later time.

The term pressure sensor as used in the present application is understood to include generally sensors which provide a pressure signal from which the blood pressure prevailing in the human limb can be determined. It may also include an optical sensor, for example, an infrared sensor, which is capable of detecting the pulse rate optically, hence enabling the cuff internal pressure to be detected from the variation of the signal with time.

The invention claimed is:

1. A method of measuring blood pressure using a wrist sphygmomanometer including a body and including a cuff attached to the body and wrapped around the wrist, said body being attached to the cuff in a manner to allow the body to be located on a thumb side of an arm when the wrist sphygmomanometer is fitted on the wrist, comprising:
    fitting the wrist sphygmomanometer on a subject's wrist;
    placing the wrist with the wrist sphygmomanometer fitted thereon on the subject's chest; and
    reading a value detected by the wrist sphygmomanometer with the wrist placed on the chest, wherein a positioning system provides a first signal that indicates that the sphygmomanometer is at an appropriate measuring level and a second signal that guides the subject to the appropriate measuring level.

2. The method of measuring blood pressure of claim 1, wherein the first signal is an acoustic signal.

3. The method of measuring blood pressure of claim 1, wherein the first signal is a visual signal.

4. The method of measuring blood pressure of claim 3, wherein the first signal includes a red light indicating an inappropriate measuring level and a green light indicating an appropriate measuring level.

5. The method of measuring blood pressure of claim 1, wherein the first signal is provided at the start of, or during blood pressure measurement.

6. The method of measuring blood pressure of claim 1, wherein the second signal includes displaying arrows that guide a user to the appropriate measuring level.

7. The method of measuring blood pressure of claim 1, wherein the second signal includes a flashing light that guides a user to the appropriate measuring level.

8. A method of measuring blood pressure of a user using a wrist sphygmomanometer including a body, and a cuff attached to the body, comprising:
    fitting the wrist sphygmomanometer on the user's wrist including locating the body on a thumb side of the user's arm;
    placing the wrist on the user's chest; and
    reading a value detected by said wrist sphygmomanometer with the wrist placed on the chest; and
    prompting the user to adopt an appropriate measuring position including displaying a visual signal on the display that guides the user to an appropriate measuring position.

9. The method of claim 8, wherein the visual signal includes arrows that guide the user to an appropriate measuring level.

* * * * *